(12) United States Patent
Cha

(10) Patent No.: US 11,331,126 B2
(45) Date of Patent: May 17, 2022

(54) SURGICAL TOOL HANDLE DEVICE

(71) Applicant: CUREXO, INC., Seoul (KR)

(72) Inventor: Yong Yeob Cha, Seoul (KR)

(73) Assignee: CUREXO, INC., Seoul (KR)

( * ) Notice: Subject to any disclaimer, the term of this patent is extended or adjusted under 35 U.S.C. 154(b) by 0 days.

(21) Appl. No.: 17/438,026

(22) PCT Filed: Mar. 13, 2020

(86) PCT No.: PCT/KR2020/003529
§ 371 (c)(1),
(2) Date: Sep. 10, 2021

(87) PCT Pub. No.: WO2020/185032
PCT Pub. Date: Sep. 17, 2020

(65) Prior Publication Data
US 2022/0039844 A1    Feb. 10, 2022

(30) Foreign Application Priority Data

Mar. 13, 2019  (KR) .......................... 10-2019-0028625

(51) Int. Cl.
*A61B 17/17* (2006.01)
*A61B 17/70* (2006.01)
*A61B 90/00* (2016.01)
*A61B 90/50* (2016.01)
*A61B 17/00* (2006.01)

(52) U.S. Cl.
CPC .......... *A61B 17/7083* (2013.01); *A61B 90/39* (2016.02); *A61B 90/50* (2016.02); *A61B 2017/0046* (2013.01); *A61B 2017/00477* (2013.01); *A61B 2017/00876* (2013.01); *A61B 2090/3937* (2016.02)

(58) Field of Classification Search
CPC .................................................. A61B 17/7083
See application file for complete search history.

(56) References Cited

U.S. PATENT DOCUMENTS

| | | | | |
|---|---|---|---|---|
| 5,305,203 A * | 4/1994 | Raab | ...................... | A61B 17/00 606/1 |
| 5,441,059 A | 8/1995 | Dannan | | |
| 6,021,343 A * | 2/2000 | Foley | ...................... | A61B 17/16 600/417 |
| 6,190,395 B1 * | 2/2001 | Williams | ............... | A61B 90/36 600/424 |
| 6,468,202 B1 * | 10/2002 | Irion | ...................... | A61B 5/064 600/112 |

(Continued)

FOREIGN PATENT DOCUMENTS

KR    10-2015-0103583 A    9/2015

*Primary Examiner* — Zade Coley
(74) *Attorney, Agent, or Firm* — Novick, Kim & Lee, PLLC; Jae Youn Kim; Jihun Kim

(57) ABSTRACT

The disclosure relates to a handle device for a surgical tool, and more particularly to a handle device for a surgical tool, which is freely controllable and usable in a surgical operation because the surgical tool is supported while steadily maintaining a position of a marker.

The handle device for the surgical tool according to the disclosure includes a handle body formed with a tool insertion hole for inserting the surgical tool therein; a grip member detachably installed in the handle body; and a marker member installed in the handle body.

6 Claims, 5 Drawing Sheets

(56) References Cited

U.S. PATENT DOCUMENTS

| | | | |
|---|---|---|---|
| 6,478,802 B2 * | 11/2002 | Kienzle, III | A61B 17/1703 |
| | | | 600/414 |
| 6,725,080 B2 * | 4/2004 | Melkent | A61B 5/06 |
| | | | 600/424 |
| 6,887,245 B2 * | 5/2005 | Kienzle, III | A61B 90/36 |
| | | | 606/80 |
| 7,877,890 B2 * | 2/2011 | Weber | A61B 90/39 |
| | | | 33/613 |
| 7,881,770 B2 * | 2/2011 | Melkent | A61B 90/11 |
| | | | 600/424 |
| 8,961,500 B2 * | 2/2015 | Dicorleto | A61B 34/20 |
| | | | 606/1 |
| 9,050,108 B2 * | 6/2015 | Grinberg | A61B 1/00064 |
| 9,161,799 B2 * | 10/2015 | Benson | A61B 17/17 |
| 2004/0171930 A1 * | 9/2004 | Grimm | A61B 17/1703 |
| | | | 600/424 |
| 2005/0154296 A1 * | 7/2005 | Lechner | A61B 17/00234 |
| | | | 600/429 |
| 2010/0107828 A1 * | 5/2010 | Huerta | B25G 1/063 |
| | | | 81/177.9 |
| 2016/0143649 A1 * | 5/2016 | Weekes | A61B 17/1622 |
| | | | 606/80 |
| 2016/0220320 A1 | 8/2016 | Nobert et al. | |
| 2018/0311051 A1 * | 11/2018 | Donaldson | A61F 2/4611 |

* cited by examiner

SURGICAL TOOL HANDLE DEVICE

TECHNICAL FIELD

The disclosure relates to a handle device for a surgical tool, and more particularly to a handle device for a surgical tool, which is freely controllable and usable in a surgical operation because the surgical tool is supported while steadily maintaining a position of a marker.

BACKGROUND ART

When a spine is damaged by an accident, etc. or damaged or twisted by degenerative diseases or wrong postures, the spine generally compresses adjacent nerves and causes severe pain. Physical therapy is available in case of minor pain, but surgery is needed in case of the severe pain so as to correct a position of a spine by inserting a fixing device for pedicle fixation or relieve a compressed nerve.

A pedicle screw insertion surgery is to perform spinal fusion by inserting a pedicle screw into a plurality of pedicles, and coupling the pedicle screw and an adjacent pedicle screw by a rod, so that the spines can be corrected to widen a distance between a pedicle compressing a nerve and an adjacent pedicle, thereby preventing the pedicle from compressing the nerve.

Further, the pedicle screw insertion surgery is carried out in such a manner that a pedicle screw is inserted into a plurality of pedicles by a fastening tool, which is called a driver, and then the rod is coupled between the screw heads of the pedicle screws.

The pedicle screw insertion surgery is generally performed relying upon medical personnel, but research has recently been carried out to partially introduce or use a surgical robot in the pedicle screw insertion surgery. For example, the pedicle screw insertion surgery may be performed by medical personnel after a robot arm of the surgical robot is put in position for the surgery and a surgical tool is mounted to an end effector of the robot arm In various orthopedic operations such as the pedicle screw insertion surgery using the surgical robot, a marker may be installed in the surgical tool to accurately perform a surgical operation. Such a marker is installed to face the surgical tool so that the marker can be recognized by an optical tracking system (OTS). Therefore, it is possible to calculate and check an endpoint location of the tool, an insertion depth, location, etc. of the pedicle screw, based on change in the position of the marker.

However, if the driver or the like surgical tool installed with the marker is rotated or moved for a surgical operation, the position of the marker is also changed and it is therefore impossible to perform an accurate surgical operation. Further, when the marker is installed in the surgical tool, a surgical operation is not smoothly carried out because of interference or unsafe gripping. Accordingly, there has been required a handle device by which a surgical operation is accurately performed and a surgical process is conveniently carried out because the position of the marker is not changed even though the surgical tool moves during the surgical operation.

DISCLOSURE

Technical Problem

Accordingly, the disclosure is conceived based on the foregoing disadvantages, and an aspect of the disclosure is to provide a handle device for a surgical tool, which is freely controllable and usable in a surgical operation because the surgical tool is supported while steadily maintaining a position of a marker.

Technical Solution

According to an aspect of the disclosure, there is provided a handle device for a surgical tool, including: a handle body formed with a tool insertion hole for inserting the surgical tool therein; a grip member detachably installed in the handle body; and a marker member installed in the handle body.

The handle body may include: a tool insertion portion in which the surgical tool is inserted in position; and a grip insertion portion formed with a plurality of grip coupling holes, in which the grip member is inserted, along a circumference of the tool insertion portion.

The grip member may include a grip to be gripped by a user; and a coupling projection protruding from the grip to be inserted in the grip coupling hole, and the handle device may include a separation preventer formed in a coupling portion and preventing the grip member coupled to the grip coupling hole from separation.

The separation preventer may include: a stopper insertion hole formed in the coupling projection; a stopper member including a ball housing to be inserted in the stopper insertion hole, a ball to be inserted in the ball housing, and an elastic member inserted in the ball housing and applying elasticity to the ball; and a locking hole formed in the grip coupling hole and locking the ball thereto.

Further, the separation preventer may include a permanent magnet placed in at least one of the grip coupling hole and the coupling projection.

The marker member may include: a marker rod including a first end to be inserted in and fastened to a marker insertion hole formed in the grip insertion portion; a marker installation member formed in a second end of the marker rod; and a plurality of markers installed in the marker installation member.

The handle device for the surgical tool may further include a tool support member installed in the handle body and movable inwards and outwards in a direction of the tool insertion hole.

The tool support member may include a tool insertion portion to which a control tool is fitted, a threaded portion extended from the tool insertion portion and fastened to a fastening hole formed in the handle body, and a surgical tool supporter extended from the threaded portion and movable inwards and outwards in the direction of the tool insertion hole.

Advantageous Effects

In a handle device for a surgical tool according to the disclosure, the surgical tool is stably supported, and the position of the marker is steadily maintained even though the surgical tool moves, so that an optical tracking system can accurately obtain position information because position change is prevented, thereby having effects on safely and accurately carrying out a surgical operation based on the position or the like of the surgical tool.

Further, in a handle device for a surgical tool according to the disclosure, a grip member is detachably installed to the handle body, so that the position of the grip member is freely changeable based on various variables or conditions in the state that a marker is facing toward the optical tracking system, thereby allowing the surgical tool to be easily gripped, and conveniently and safely carrying out a surgical operation.

DESCRIPTION OF DRAWINGS

FIGS. 5 and 6 are views for describing operations of a handle device for a surgical tool according to an embodiment of the disclosure, in which FIG. 5 is a perspective view showing that the surgical tool is mounted to the handle device, and FIG. 6 illustrates that the handle device mounted with the surgical tool is installed in a surgical robot.

MODE FOR INVENTION

Below, embodiments of the disclosure will be described with reference to the accompanying drawings of FIGS. 1 to 6, in which like numerals refer to like elements throughout.

Further, detailed descriptions about elements and their operations and effects, which are easily understood by a person having ordinary knowledge in the art from general technology, in the accompanying drawings will be simplified or omitted. In addition, the disclosure is characterized in a handle device for a surgical tool, and thus illustration and description will be made focusing on related parts while simplifying or omitting the other parts.

Figure 1:
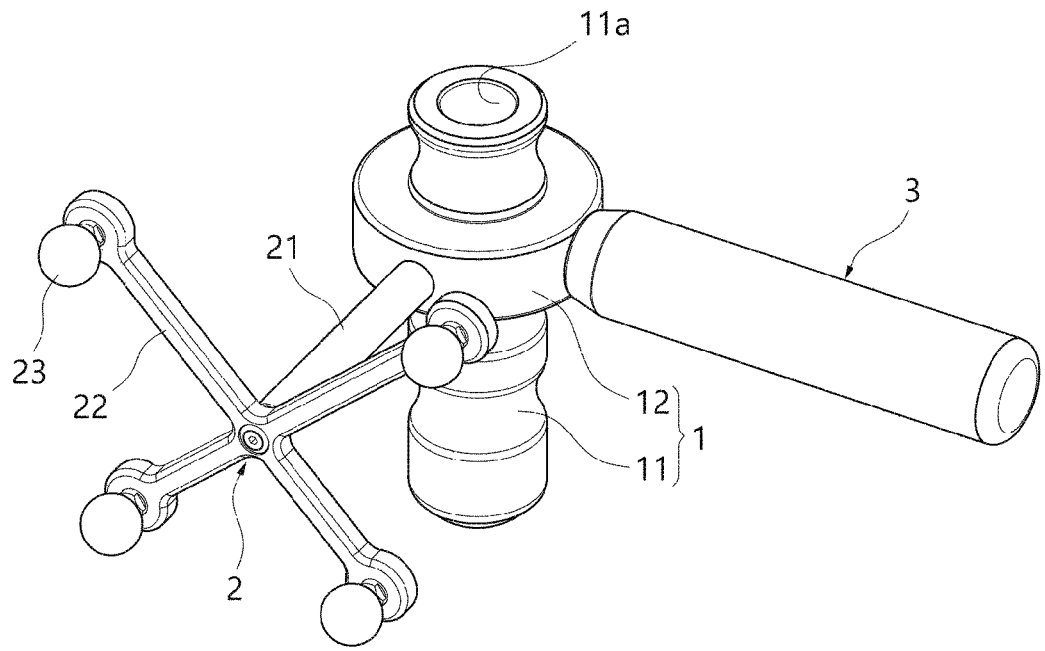
FIG. 1 is a perspective view of a handle device for a surgical tool according to an embodiment of the disclosure.
Figure 2:
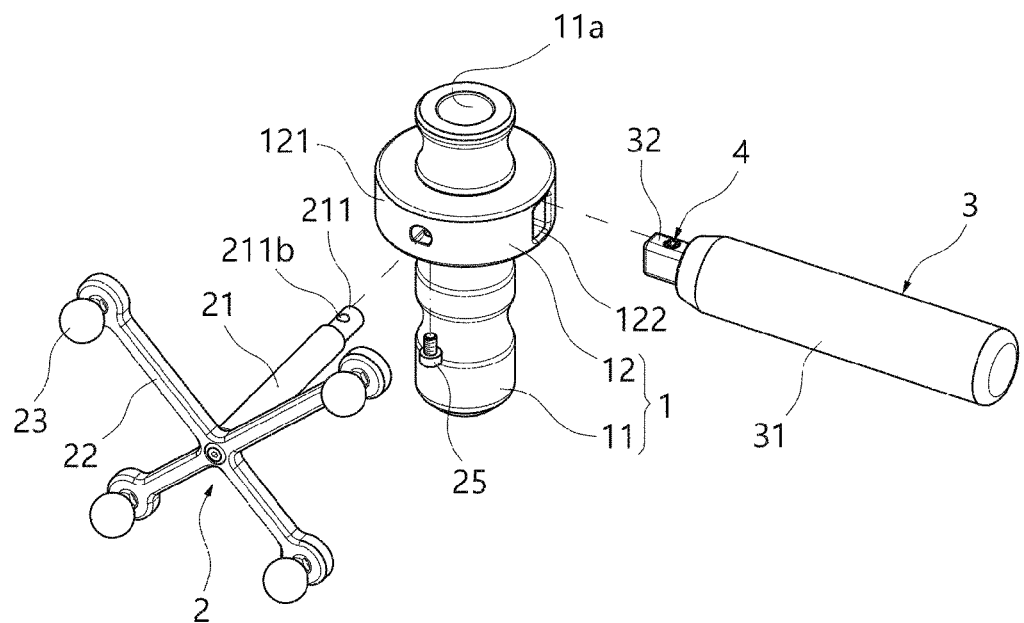
FIG. 2 is an exploded perspective view of a handle device for a surgical tool according to an embodiment of the disclosure.
Figure 3:
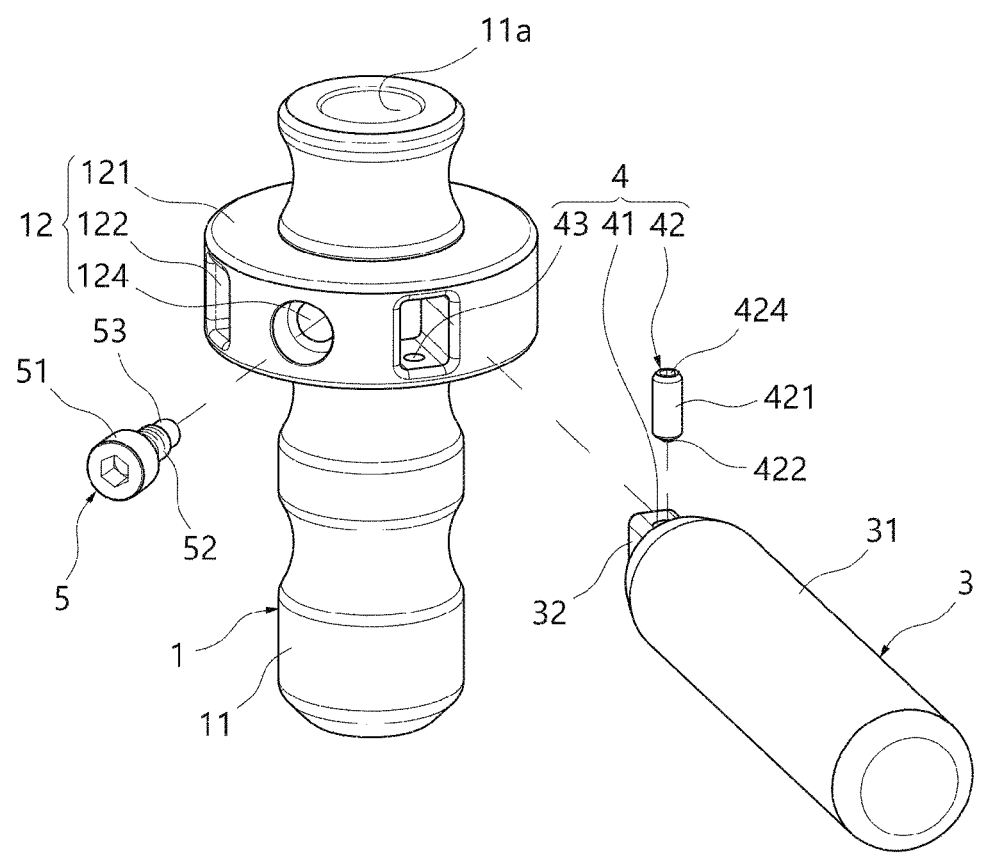
FIG. 3 is a partial exploded perspective view for describing a detachable structure of a grip member in a handle device for a surgical tool according to an embodiment of the disclosure.

FIG. 1 is a perspective view of a handle device for a surgical tool according to an embodiment of the disclosure, FIG. 2 is an exploded perspective view of a handle device for a surgical tool according to an embodiment of the disclosure, and FIG. 3 is a partial exploded perspective view for describing a detachable structure of a grip member in a handle device for a surgical tool according to an embodiment of the disclosure.

Referring to FIGS. 1 to 3, a handle device for a surgical tool according to an embodiment of the disclosure is characterized in that a marker position is not changed even through the surgical tool t moves, and includes a handle body 1, a marker member 2 and a grip member 3.

The handle body 1 refers to an element that functions as a body to which the surgical tool t is mounted, and has a bar-shaped body internally formed with a tool insertion hole 11a in which the surgical tool is inserted along a lengthwise direction.

Further, the handle body 1 includes a tool insertion portion 11 into which the surgical tool is inserted in position, and a grip insertion portion 12 provided in the tool insertion portion 11 so that the grip member 3 can be inserted in the grip insertion portion 12.

The tool insertion portion 11 has a structure that the tool insertion hole 11a is formed in the bar-shaped body having a plurality of uneven portions, but the tool insertion portion 11 may have various structures according to the shape or the like of the surgical tool without limitations.

The grip insertion portion 12 includes an insertion main body 121 formed on the outer side of the tool insertion portion 11, and a plurality of grip coupling holes 122 formed to insert the grip member 3 therein along the circumference of the insertion main body 121.

The insertion main body 121 may, but not limited to, protrude in the form of a disc so that the grip member 3 can be easily attached and detached thereto, and its protruding position may be at a predetermined distance downward from the top of the handle body 1 so as not to interfere with the surgical tool being attached and detached.

Further, there are no limits to the number and orientation of grip coupling holes 122. In this embodiment, three grip coupling holes 122 are formed in the insertion main body at equiangular intervals of 90° so that a user can freely select a gripping direction among three directions in the state that the marker member 2 is disposed facing toward an optical tracking system.

The grip member 3 refers to an element that is detachably installed in the handle body 1, and includes a grip 31 to be gripped by a user, and a coupling projection 32 protruding from the grip 31 to be inserted in the grip coupling hole 122.

In the handle device for the surgical tool according to the disclosure, the grip member 3 may have a detachable structure for being forcibly fitted to and pulled and separated from the handle body 1. However, according to this embodiment, there is a separation preventer 4 for smooth and stable detachable-operation.

The separation preventer 4 is provided in the coupling portion of the grip member 3 so as to prevent the grip member 3 coupled to the grip coupling hole 122 from being easily separated.

In more detail, the separation preventer 4, as shown in FIG. 3, includes a stopper insertion hole 41 formed in the coupling projection 32, a stopper member 42 installed in the stopper insertion hole 41, and a locking hole 43 formed in the grip coupling hole 122 so that the stopper member 42 is locked thereto.

The stopper member 42 includes a ball housing 421 inserted in the stopper insertion hole 41, a ball 422 inserted in the ball housing 421 and locked to the locking hole 43 when the grip member 3 is fastened, an elastic member (not shown) inserted in the ball housing 421 and applying elasticity to the ball 422, and a separation preventing member 424 fastened to the ball housing 421.

Further, besides the stopping structure based on the foregoing ball 422, the separation preventer 4 may have various structures without any specific limits as long as it can prevent the grip member 3 coupled to the grip coupling hole 122 from being separate.

For example, the separation preventer 4 may be achieved by installing a permanent magnet to at least one of the grip coupling hole and the coupling projection when the handle body 1 and the grip member 3 include a magnetic substance.

Figure 4:
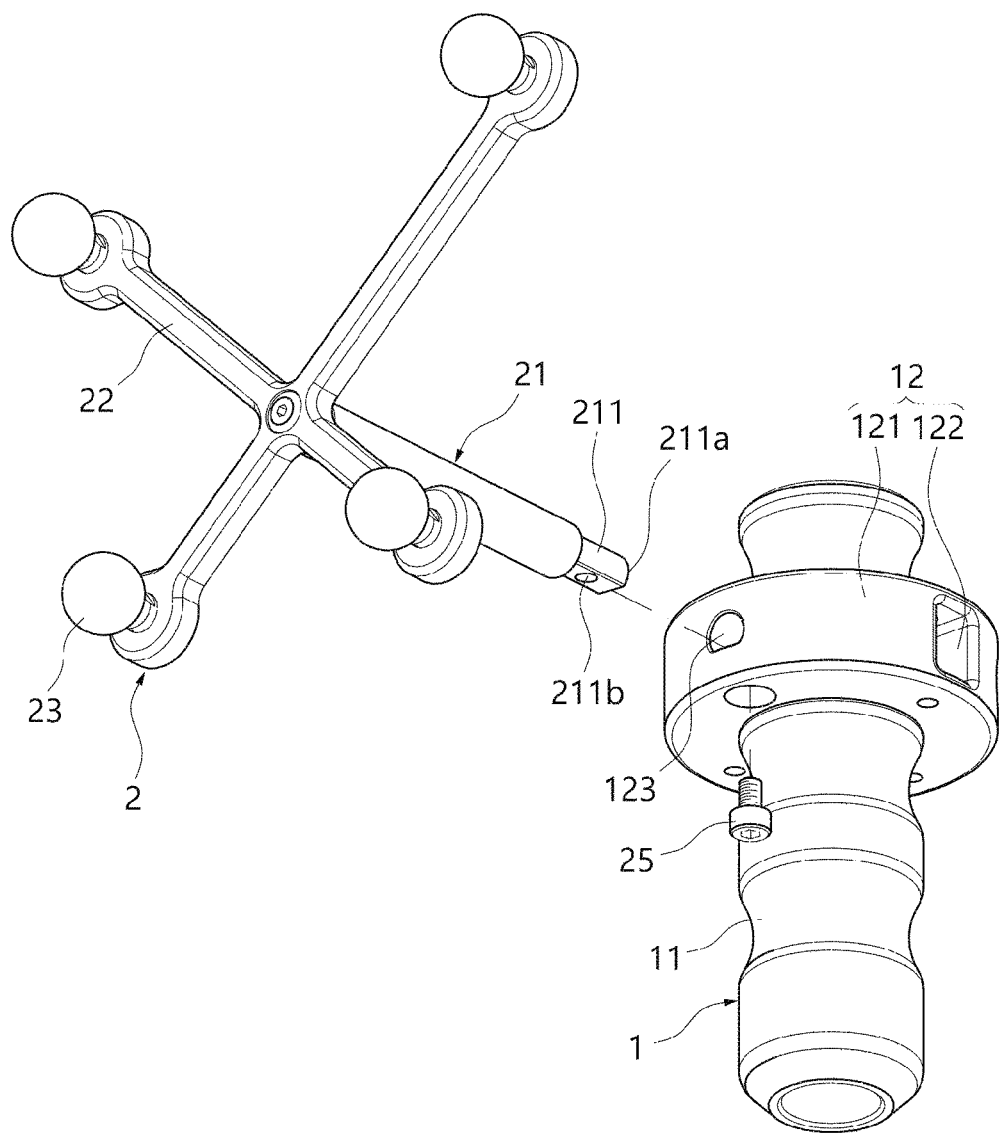
FIG. 4 is a partial exploded perspective view for describing a detachable structure of a marker member in a handle device for a surgical tool according to an embodiment of the disclosure.

FIG. 4 is a partial exploded perspective view for describing a detachable structure of a marker member in a handle device for a surgical tool according to an embodiment of the disclosure.

Referring to FIG. 4, the marker member 2 refers to an element to be installed in the handle body 1, and includes a marker rod 21 having a first end to be inserted in and fastened to a marker insertion hole 123 formed in a grip insertion portion 121, a marker installation member 22 formed in a second end of the marker rod 21, and a plurality of markers 23 installed in the marker installation member 22. Here, the marker insertion hole 123 is formed as a groove having a cross-section approximately shaped like 'D.' Further, the marker 23 is to provide reflected light to the optical tracking system (OTS) and obtain position information through a calculation process, and is achieved by a publicly-known common marker.

The marker rod 21 is formed with a rod coupling portion 211 which is cut in the form of 'D' in a portion to be inserted in the marker insertion hole 123, thereby having a spin-preventing surface. Further, the rod coupling portion 211 is formed with a fastening hole 211b in which a fastening bolt 25 is inserted when fastened.

In addition, the handle device for the surgical tool according to the disclosure includes a tool support member 5 installed in the handle body 1 and supporting the surgical tool inserted in the direction of the tool insertion hole 11a.

For example, the tool support member 5 is retractably installed in the fastening hole 124 formed in the insertion main body 121, and includes a tool insertion portion 51 into which an Allen wrench or the like tool is fitted, a threaded portion 52 extended from the tool insertion portion 51 and fastened to the fastening hole 124 formed in the insertion main body 121, and a surgical tool supporter 53 extended from the threaded portion 52 and moves inwards and outwards in the direction of the tool insertion hole 11a.

Below, operations of a handle device for a surgical tool according to an embodiment of the disclosure will be described in short.

Figure 5:
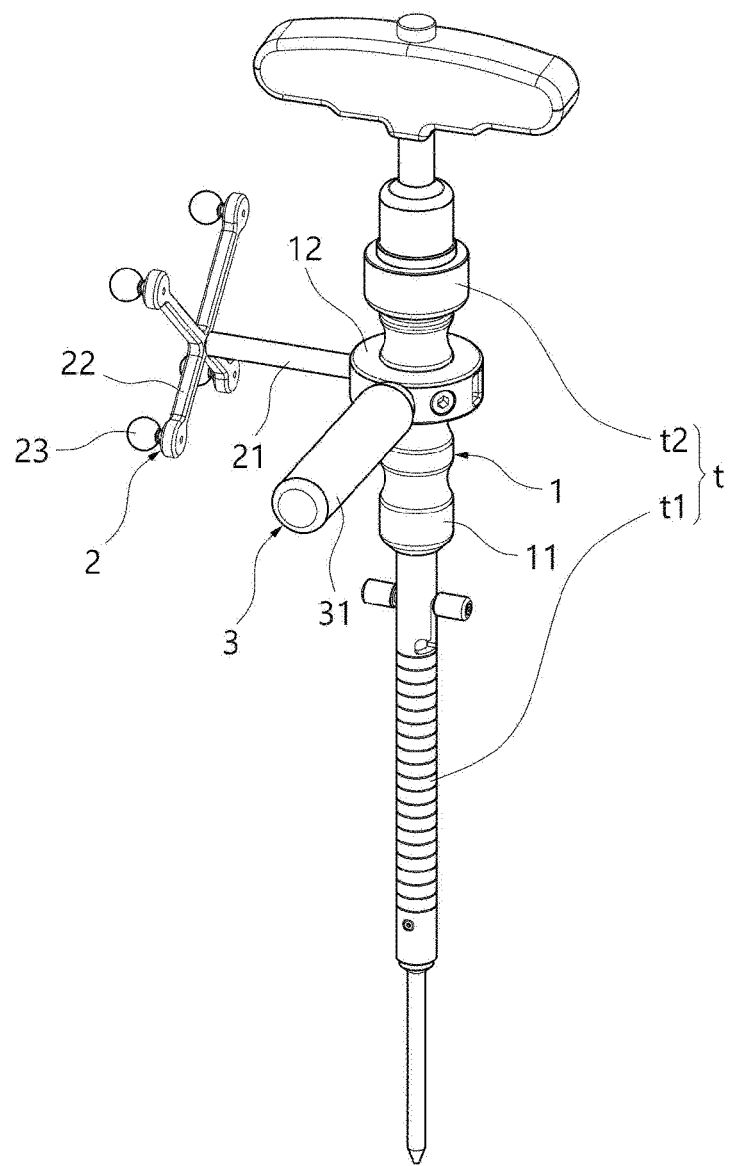
Figure 6:
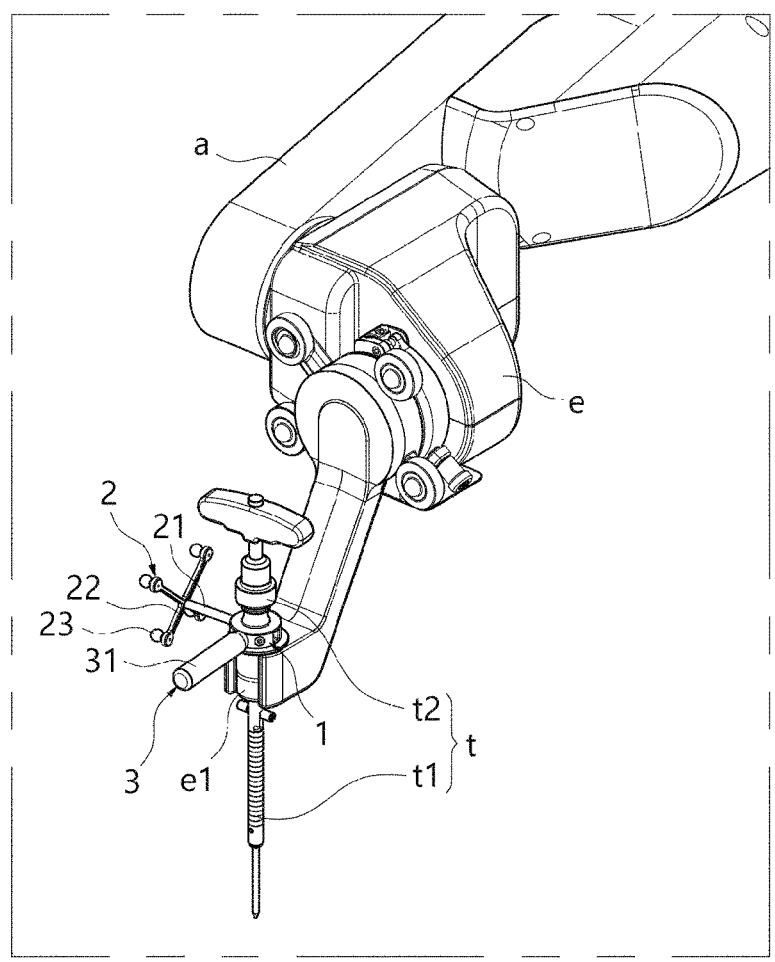

FIGS. 5 and 6 are views for describing operations of a handle device for a surgical tool according to an embodiment of the disclosure, in which FIG. 5 is a perspective view showing that the surgical tool is mounted to the handle device, and FIG. 6 illustrates that the handle device mounted with the surgical tool is installed in a surgical robot.

As shown in FIG. 5, the handle device for the surgical tool according to the disclosure is installed in an end effector e provided in a robot arm a of a surgical robot in the state that the screw surgical device t1 and the control tool t2 are coupled. Here, the end effector e includes a surgical tool holder e1 approximately shaped like a bushing and inserted in the end of a guide member formed like an inclined bar, and the handle device for the surgical tool is inserted and supported in the surgical tool holder e1.

Further, there are no specific limits to the kind or shape of the surgical tool t installed in the surgical tool handle device. For example, the surgical tool t according to this embodiment includes the screw surgical device t1 that performs a reaming process and a tapping process with regard to a pedicle, and a process of inserting a pedicle screw into the pedicle during the pedicle screw insertion surgery, and the control tool t2 for controlling the screw surgical device t1.

As described above, in the state that the handle device with the surgical tool t is mounted to the robot arm a, and the marker member 2 is in position to face toward and be scanned by the optical tracking system (OTS, not shown), the surgical tool t is controlled to perform a surgical operation. In this case, a user can turn the control tool t2 with one hand while gripping the grip member 3 with the other hand, thereby smoothly turning only the control tool t2 without turning the handle device for the surgical tool. Therefore, the marker member 2 fastened to the handle body 1 is not turned but maintained facing toward the optical tracking system, thereby allowing the optical tracking system (OTS) to stably receive reflected light from the marker 23 and continuously obtain position information based on a calculation process.

Further, as described above, when the gripping position of the handle device for the surgical tool is needed to be changed as a patient or user's surgical site or the like condition is changed in a surgical process, the gripping position is changeable in such a manner that the grip member 3 is pulled out and separated from the grip insertion portion 12 and then inserted again into the grip coupling hole 122 at a position convenient for the surgical operation.

As described above, in a handle device for a surgical tool according to an embodiment of the disclosure, the surgical tool t is rotatably installed in the handle device, and therefore the position of the marker is steadily maintained even though the surgical tool t is turned, thereby easily and safely carrying out the surgical operation while changing the position of the grip member 3 as necessary.

Although the features and operations of a handle device for a surgical tool according to the embodiments of the disclosure have been described above, these are for illustrative purposes only, and it is understood by a person having ordinary knowledge in the art that change or replacement can be made in the foregoing embodiments of the disclosure without departing from technical scope of the disclosure.

Therefore, it is appreciated that the scope of the disclosure falls within the appended claims and its equivalents.

INDUSTRIAL APPLICABILITY

A handle device for a surgical tool according to the disclosure, which is freely controllable and usable in a surgical operation because the surgical tool is supported while steadily maintaining a position of a marker, may be employed as a surgical tool handle device for a pedicle screw insertion surgery.

The invention claimed is:
1. A handle device for a surgical tool, comprising:
a handle body having a tool insertion hole formed therethrough for holding the surgical tool inserted into the insertion hole;
a grip member detachably coupled to the handle body; and
a marker member coupled to the handle body,
wherein the handle body comprises a tool insertion portion in which the surgical tool is placed in position, and a grip insertion portion having a plurality of grip coupling holes formed along a circumference of the grip insertion portion, the grip member being coupled to one of the plurality of grip coupling holes,
wherein the grip member comprises a grip configured to be gripped by a user, and a coupling projection protruding from the grip to be inserted into one of the plurality of grip coupling holes,
wherein the handle device further comprises a separation preventer for preventing the grip member coupled to one of the plurality of grip coupling holes from being separated,
wherein the separation preventer comprises a stopper insertion hole formed in the coupling projection, a ball housing configured to be inserted in the stopper insertion hole, a ball coupled with the ball housing, and an elastic member disposed in the ball housing and applying elasticity to the ball, and a locking hole formed in the respective grip coupling hole for receiving the ball therein, or wherein the separation preventer comprises a magnet placed in at least one of the respective grip coupling hole and the coupling projection,
wherein the grip insertion portion comprises an insertion main body surrounding an outer side of the tool insertion portion, the plurality of grip coupling holes being formed along a circumference of the insertion main body, wherein the insertion main body has a disc-shaped body protruding from the tool insertion portion so that the grip member is attached to or detached therefrom, and wherein the insertion main body is positioned at a predetermined distance downward from a top of the tool insertion portion to avoid an interference with the surgical tool when the surgical tool is coupled to or decoupled from the tool insertion portion.

2. The handle device for the surgical tool of claim 1, wherein the marker member comprises:

a marker rod having a first end configured to be inserted in and fastened to a marker insertion hole formed in the grip insertion portion;

a marker installation member coupled with a second end of the marker rod; and a plurality of markers disposed on the marker installation member.

3. The handle device for the surgical tool of claim 2, wherein the marker insertion hole is a groove having a cross-section shaped of 'D', and wherein the marker rod comprises a rod coupling portion cut in the form of 'D' and having a spin-preventing surface, and a fastening hole into which a fastening bolt is inserted when coupled to the rod coupling portion.

4. The handle device for the surgical tool of claim 1, further comprising a tool support member disposed in the handle body to be movable inwards and outwards in a direction of the tool insertion hole.

5. The handle device for the surgical tool of claim 4, wherein the tool support member comprises a tool insertion head to which a control tool is fitted, a threaded portion extended from the tool insertion head to be fastened to a fastening hole formed in the handle body, and a surgical tool supporter extended from the threaded portion and movable inwards and outwards in the direction of the tool insertion hole.

6. The handle device for the surgical tool of claim 1, wherein the tool insertion portion has a bar-shaped body having a plurality of uneven portions.

\* \* \* \* \*